US009023314B2

(12) United States Patent
O'Neil

(10) Patent No.: US 9,023,314 B2
(45) Date of Patent: May 5, 2015

(54) SURFACE TREATMENT FOR A MEDICAL DEVICE

(75) Inventor: Michael P. O'Neil, Dublin, CA (US)

(73) Assignee: Covidien LP, Mansfield, MA (US)

( * ) Notice: Subject to any disclaimer, the term of this patent is extended or adjusted under 35 U.S.C. 154(b) by 992 days.

(21) Appl. No.: 12/570,508

(22) Filed: Sep. 30, 2009

(65) Prior Publication Data

US 2010/0139663 A1    Jun. 10, 2010

Related U.S. Application Data

(60) Provisional application No. 61/101,245, filed on Sep. 30, 2008.

(51) Int. Cl.
  A61K 49/00    (2006.01)
  A61M 16/04    (2006.01)
  C08J 7/12     (2006.01)

(52) U.S. Cl.
  CPC ....... *A61M 16/04* (2013.01); *A61M 2205/0233* (2013.01); *C08J 7/12* (2013.01)

(58) Field of Classification Search
  None
  See application file for complete search history.

(56) References Cited

U.S. PATENT DOCUMENTS

| | | | |
|---|---|---|---|
| 3,412,729 | A |  | 11/1968 | Smith, Jr. |
| 4,830,014 | A |  | 5/1989 | Goodman et al. |
| 5,213,099 | A |  | 5/1993 | Tripp, Jr. |
| 5,217,492 | A | * | 6/1993 | Guire et al. ............. 600/36 |
| 5,368,025 | A |  | 11/1994 | Young et al. |
| 5,551,423 | A |  | 9/1996 | Sugiura |
| 5,784,151 | A |  | 7/1998 | Miller et al. |
| 5,800,349 | A |  | 9/1998 | Isaacson et al. |
| 6,454,718 | B1 |  | 9/2002 | Clift |
| 6,470,199 | B1 |  | 10/2002 | Kopotic et al. |
| 6,629,924 | B2 |  | 10/2003 | Aydelotte |
| 6,694,180 | B1 |  | 2/2004 | Boesen |
| 6,735,459 | B2 |  | 5/2004 | Parker |
| 6,976,963 | B2 |  | 12/2005 | Clift |
| 7,341,559 | B2 |  | 3/2008 | Schulz et al. |
| 7,606,606 | B2 |  | 10/2009 | Laakkonen |
| 2003/0199945 | A1 |  | 10/2003 | Ciulla |
| 2005/0209516 | A1 |  | 9/2005 | Fraden |
| 2006/0178430 | A1 |  | 8/2006 | Blackwell et al. |
| 2007/0161949 | A1 | * | 7/2007 | Knox et al. ............. 604/93.01 |
| 2007/0185393 | A1 |  | 8/2007 | Zhou et al. |
| 2008/0051670 | A1 |  | 2/2008 | Banet et al. |
| 2008/0058614 | A1 |  | 3/2008 | Banet et al. |

OTHER PUBLICATIONS

Oosterhof JJ, Buijssen KJ, Busscher HJ, van der Laan BF, van der Mei HC. Effects of quaternary ammonium silane coatings on mixed fungal and bacterial biofilms on tracheoesophageal shunt prostheses. 2006 Appl. Environ. Microbiol. 72: 3673-3677.*
Dell'Acqua G, Giacometti A, Cirioni O, Ghiselli R, Saba V, Scalise G, Gov Y, Balaban N. Suppression of drug-resistant Staphylococcal Infections by the quorum-sensing inhibitor RNAIII-inhibiting peptide. 2004 J. Infect. Dis. 190: 318-320.*
Shaw JF, Chang RC, Wang FF, Wang YJ. Lipolytic activities of a lipase immobilized on six selected supporting materials. 1990 Biotechnol. Bioeng. 35: 132-137.*
Janssens JC, Metzger K, Daniels R, Ptacek D, Verhoeven T, Habel LW, Vanderleyden J, De Vos DE, De Keersmaecker SC. Synthesis of N-acyl homoserine lactone analogues reveals strong activators of SdiA, the *Salmonella enterica* serovar Typhimurium LuxR homologue. 2007 Appl. Environ. Microbiol. 73: 535-544.*
Goddard et al. Polymer surface modification for the attachment of bioactive compounds. 2007 Prog. Polym. Sci. 32: 698-725.*
Geske, Grant D. et al., Small Molecule Inhibitors of Bacterial Quorum Sensing and Biofilm Formation, J. Am. Chem. Soc., 2005, 127, 12762-12763.
Kollef M; Afessa B; Anzueto A; Veremakis C; Kerr KM; Margolis BD; Craven DE; Roberts PR; Arroliga AC; Hubmayr RD; Restrepo MI; Auger WR; Dipl-Stat RS Silver-coated endotracheal tubes and incidence of ventilator-associated pneumonia: The nascent randomized trial, The Journal of the American Medical Association 805-813 300(7) Aug. 20, 2008.
Shintani 2004 Trends in Biomaterials & Artificial Organs 1-8 18(1) Dec. 31, 2004 Shintani H Modification of medical device surface to attain anti-infection.
NCT00341354 National Heart, Lung, and Blood Institute (NHLBI) Jun. 19, 2006 NHLBI Evaluation of Silver-Sulfadiazine Tracheal Tubes/Mucus Shaver in Intubated Patients Expected to Have a Prolonged Mechanical Ventilation.
Agento I.C. Endotracheal Tube C, R. Bard http://www.bardmedical.com/products/loadProduct.aspx?prodID=391 , (copyright 2007).
Sheridan Laser-TRACH (copyright 2004)Teleflex Medical—Hudson RCI http://www.hudsonrci.com/Products/product_results.asp?catalog=1[]_cat=21[]_subcat=38.
U.S. Appl. No. 11/275,896, filed Feb. 2, 1996, Blackwell, H.E.

* cited by examiner

*Primary Examiner* — Michael G Hartley
*Assistant Examiner* — Jennifer Lamberski
(74) *Attorney, Agent, or Firm* — Fletcher Yoder PC

(57) ABSTRACT

A surface coating for a medical device is provided that may prevent or slow the formation of medical biofilms on the surface of the device. Covalent attachment of certain analogues of N-acyl L-homoserine lactones onto a medical device may provide the advantage of slowing biofilm formation in a manner that is targeted to the surface of the medical device and not the patient. Such a device may allow healthcare providers to prevent bacterial buildups on the surfaces of the device, which may lead to biofilm formation.

15 Claims, 2 Drawing Sheets

SURFACE TREATMENT FOR A MEDICAL DEVICE

RELATED APPLICATION

This application claims priority to U.S. Provisional Application No. 61/101,245, filed Sep. 30, 2008, and is incorporated herein by reference in its entirety.

BACKGROUND

The present disclosure relates generally to medical devices and, more particularly, to surface treatments to prevent the formation of biofilms on medical devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Advances in technology have allowed for the utilization of foreign, non-biological devices in medicine for increased external control over normal bodily functions. Such devices allow medical personnel to clearly define the environment in which the patient exists during his/her treatment as well as control, analyze, and supplement both intake and output by patients. Examples of these devices include endotracheal tubes, catheters, cardiac stunts, and the like. Endotracheal tubes may be used for patients having lengthy and complicated hospital stays to ensure adequate ventilation and/or oxygen levels for the intubated patient. Lungs have a normal microbial flora populated by both anaerobic and aerobic bacteria with a concurrent local host immune system tuned to this population and effective against normal challenges from the environment.

However, the introduction of an indwelling medical device, such as an endotracheal tube, can challenge this delicate balance. The endotracheal tube introduces a new growth surface for both foreign organisms, i.e. not in the normal flora, and even organisms present in the normal flora but whose growth is normally suppressed by the restricted growth space of the lung. The new growth surface may allow for new colonization in the lungs by such bacteria, which may be pathogenic. For example, prolonged microbial colonization may lead to biofilm formation associated with the device. A biofilm is an aggregation of microorganisms that excretes an adhesive matrix that helps to anchor the biofilm onto a surface. Biofilms may represent a continuing source of infectious bacteria that can be dislodged by patient coughing, suctioning of the device, or even simple movement of the device itself.

The prevention of microbial colonization of indwelling medical devices may allow medical professionals to prevent subsequent biofilm formation. This prevention may result in better outcomes for a patient with an indwelling medical device.

SUMMARY

Certain aspects commensurate in scope with the present disclosure are set forth below. It should be understood that these aspects are presented merely to provide the reader with a brief summary of certain forms specific embodiments might take and that these aspects are not intended to limit the scope of the disclosure. Indeed, the disclosure may encompass a variety of aspects that may not be set forth below.

There is provided an airway device that includes a conduit for insertion into a patient's trachea; and an acyl-homoserine lactone analog covalently bound to the conduit, wherein the acyl-homoserine lactone analog is capable of reducing biofilm formation on the conduit when the conduit is inserted into the trachea.

There is also provided a method of manufacturing an airway device that includes covalently binding an acyl-homoserine lactone analog to one or more spacer molecules bound to a surface of a conduit for insertion into a patient's trachea.

There is also provided an airway device system that includes a conduit for insertion into a patient's trachea; an acyl-homoserine lactone analog covalently bound to the conduit, wherein the acyl-homoserine lactone analog is capable of reducing biofilm formation on the conduit when the conduit is inserted into the trachea; and a monitor operatively coupled to the conduit, wherein the monitor is adapted to monitor at least one characteristic of a patient.

There is also provided an airway device that includes a device body having one or more surfaces, wherein at least one surface comprises one or more compounds capable of interrupting bacterial communication, and wherein the one or more compounds are covalently attached to the surface.

BRIEF DESCRIPTION OF THE DRAWINGS

Advantages of the present techniques may become apparent upon reading the following detailed description and upon reference to the drawings in which.

DETAILED DESCRIPTION

Figure 1:
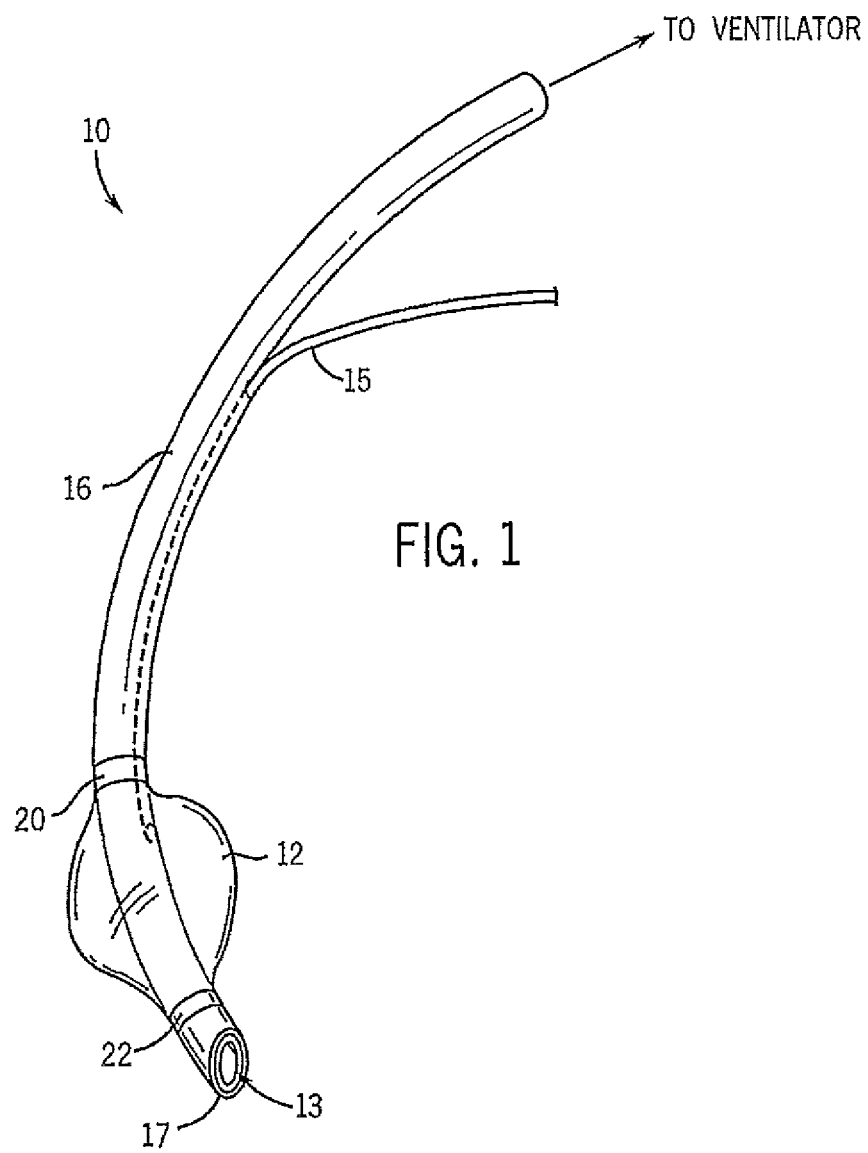
FIG. 1 illustrates an exemplary endotracheal tube that includes molecules of an acyl-homoserine lactone analog covalently bound to the conduit.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain compounds, including acyl-homoserine lactone analogs, may act to interrupt bacterial communication pathways involved in biofilm formation. Many bacteria use naturally occurring quorum-sensing compounds that include autoinducer ligands to monitor their population densities. At high cell densities, bacteria may then activate a process to promote the formation of biofilms. Synthetic analogs of chemical compounds involved in these pathways may interrupt the action of the naturally occurring compounds and prevent the signaling that leads to biofilm formation. For example, such analogs may inhibit binding of a native ligand, thus preventing activation of quorum-sensing pathways. Because such compounds inhibit biofilm formation without destroying individual bacteria in the process, these compounds are not microbicidal agents.

Provided herein are airway medical devices that include acyl-homoserine lactone analogs. Covalently attaching these compounds to a surface of a medical device may prevent or reduce formation of biofilms on the device. Such compounds that are covalently bound to the device may not be eluted or otherwise leak from the device. Accordingly, covalent attachment of these compounds to a medical device provides the advantage of harnessing the chemical functionality of these compounds without their systemic administration to a patient, Synthetic acyl-homoserine lactone analogs, which are relatively large compounds, may be sterically hindered when directly attached to the surface of a medical device. In certain embodiments, the devices provided herein include a carbon tether, which spaces the acyl-homoserine lactone analog apart from the medical device and increases chemical communication with bacteria. Changing the length of the carbon tether may improve the ability of the medical device to prevent biofilm formation, It is desirable to provide an airway device, such as an endotracheal tube or other medical device, which may prevent formation of biofilms on its surface. In certain embodiments, the present techniques may be used in conjunction with any appropriate medical device, including a feeding tube, an endotracheal tube, a tracheostomy tube, a circuit, an airway accessory, a connector, an adapter, a filter, a humidifier, a nebulizer, nasal cannula, or a laryngeal mask. The present techniques may also be useful for any patient benefiting from mechanical ventilation. Further, the devices and techniques provided herein may be useful for a human patient, such as a trauma victim, an intubated patient, a patient with a tracheostomy, an anesthetized patient, a cardiac arrest victim, a patient suffering from airway obstruction, or a patient suffering from respiratory failure.

FIG. 1 illustrates an embodiment in which an endotracheal tube 10 with covalently attached molecules of acyl-homoserine lactone analog 17 disposed on the outer surface of a conduit 16 and/or a cuff 12. The endotracheal tube 10 also includes an inflatable cuff 12 that may be inflated to form a seal against the trachea walls. Typically, the cuff 12 is disposed, adhesively or otherwise, towards the distal end 13 of the conduit 16. The cuff 12 may be inflated and deflated via an inflation lumen 15 in communication with the cuff 12, typically through a hole or a notch in the conduit 20. The cuff 12 has a proximal opening 20 and a distal opening 22 formed in the cuff walls to accommodate the conduit 16.

The covalently attached molecules of acyl-homoserine lactone analog 17 may be disposed on all or a portion of the outer surface or the inner surface of the conduit 16 or the cuff 12. The conduit 16 may be formed from materials having suitable mechanical properties (such as puncture resistance, pin hole resistance, tensile strength), chemical properties, and biocompatibility. In one embodiment, the walls of the inflatable cuff 12 are made of polyurethane having suitable mechanical and chemical properties. In another embodiment, the walls of the inflatable cuff 12 are made of a suitable polyvinyl chloride (PVC). Suitable materials may also include polyethylene teraphthalate (PETP), low-density polyethylene (LDPE), polypropylene, silicone, neoprene, or polyisoprene.

In certain embodiments, the covalently attached molecules of acyl-homoserine lactone analog 17 may include a compound having Formula (I),

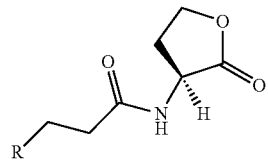

(I)

where R represents the point of covalent attachment to the conduit 16. The attachment point R may also include other moieties bound at the carbon attachment site, including,

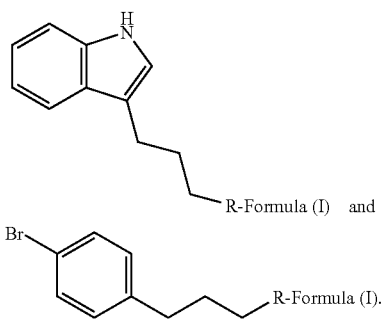

R-Formula (I) and

R-Formula (I).

In other embodiments, the covalently attached molecules of acyl-homoserine lactone analog 17 may be compounds such as those disclosed in U.S. patent application Ser. No. 11/275,896, entitled "COMPOUNDS AND METHODS FOR MODULATING COMMUNICATION AND VIRULENCE IN QUORUM SENSING BACTERIA," filed on Feb. 2, 2006, and issued as U.S. Pat. No. 7,642,285, the specification of which is incorporated by reference herein in its entirety for all purposes.

Figure 2:
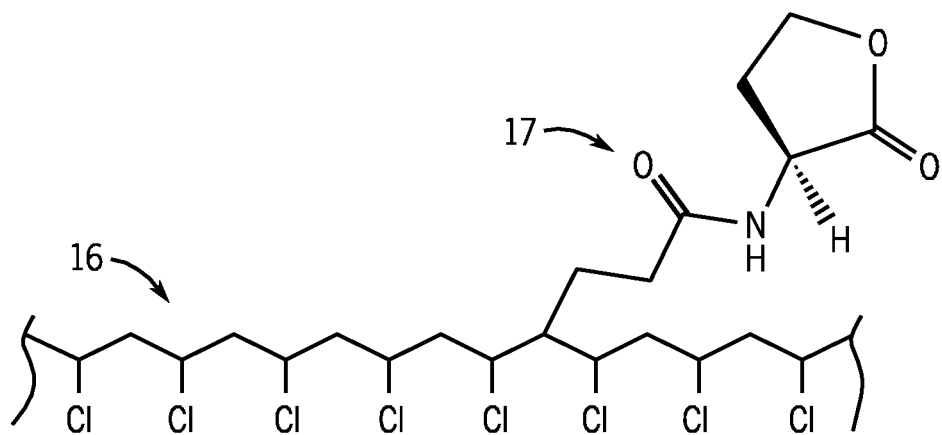
FIG. 2 illustrates an exploded view of the conduit with the acyl-homoserine lactone analog covalently bound.

FIG. 2 shows an exploded view of a surface of an exemplary conduit 16 with covalently attached molecules of acyl-homoserine lactone analog 17. As shown, the acyl-homoserine lactone analog 17 may be covalently attached at points along the carbon backbone of a PVC conduit. The acyl-homoserine lactone analog 17 is shown with a three-carbon tether. In other embodiments, the carbon backbone may have acyl-homoserine lactone analog 17 covalently bound to the backbone as in Formula (II)

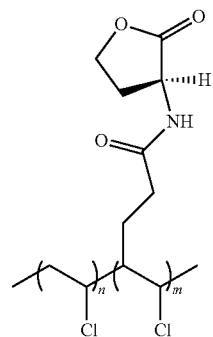

(II)

where n or m may be any number. In certain embodiments, n is greater than m. For example, in one embodiment, n is 4 and m is 1.

The conduit 16 may be functionalized with the acyl-homoserine lactone analog 17 by any suitable method. The surface treatment may include plasma treatment, corona discharge, ion implantation, ion bombardment, or treatment with chemical coupling agents (e.g. silane coupling agents, Volan), surfactants, or primers. In one embodiment, a PVC surface may be functionalized by cold plasma processing. The concentration of the acyl-homoserine lactone analog 17 added to the reactive conduit surface may be optimized for any desired spacing of the acyl-homoserine lactone analog 17 along the conduit surface.

In another implementation, molecules of acyl-homoserine lactone analogs 17 may be tethered to the surface through extended spacer chains, such as carbon tethers, which may include one or more spacer chain extender molecules, covalently bound to the substrate surface. A substrate surface may first be exposed to a plasma to produce active sites, and the active sites are then reacted with a first reactant gas of spacer molecules in situ in the absence of plasma to provide surface-bound spacer chains on the substrate surface. The surface-bound spacer chains are then reacted with a second reactant gas of spacer chain extender molecules in situ in the absence of plasma to provide an extended spacer chain. The extended spacer chain may be further extended through one or more additional extension reactions by reacting the chains with additional gas-phase spacer chain extender molecules in a series of consecutive gas phase reactions. Finally, acyl-homoserine lactone analogs 17 may be immobilized on the surface of the conduit 16 by reacting them with the terminal spacer chain extender molecules. By selecting the number and length of spacer molecules and spacer chain extender molecules that go into producing the extended spacer chains, the distance between the covalently bound acyl-homoserine lactone analogs 17 and the conduit surface may be tailored to fit a selected application.

Figure 3:
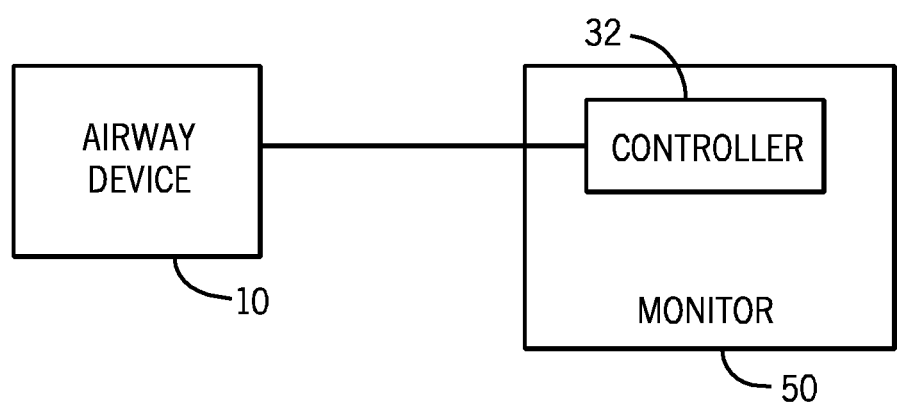
FIG. 3 is a block diagram of a system according to the present techniques.

The endotracheal tube 10 or airway devices as provided herein may be incorporated into systems that facilitate positive pressure ventilation of a patient, such as a ventilator. As illustrated in FIG. 3, these systems may include connective tubing, a gas source, a monitor 50, and/or a controller 32. The controller 32 may be a digital controller, a computer, an electromechanical programmable controller, or any other control system.

While the disclosed embodiments may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the disclosure as defined by the following appended claims.

What is claimed is:

1. An airway device comprising:
   a conduit for insertion into a patient's trachea; and
   an acyl-homoserine lactone analog comprising a hydrocarbon tether covalently bound directly to a surface of the conduit, wherein the acyl-homoserine lactone analog is a non-microbicidal compound configured to interrupt bacterial communication to reduce biofilm formation on the conduit when the conduit is inserted into the trachea, and wherein the conduit which is covalently bound to the acyl-homoserine lactone analog comprising a hydrocarbon tether has a Formula (II),

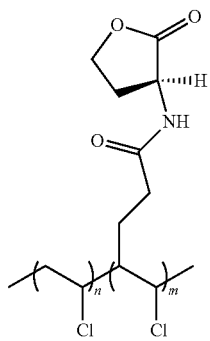

and wherein n or m is any number greater than 1.

2. The airway device recited in claim 1, wherein the airway device comprises an endotracheal tube or a tracheotomy tube.

3. The airway device recited in claim 1, wherein n is greater than m.

4. The airway device recited in claim 1, wherein n is 4 and m is 1.

5. A method of manufacturing an airway device comprising:
   activating a surface of the airway device via plasma treatment, wherein the airway device comprises a conduit for insertion into a patient's trachea;
   covalently binding at least one hydrocarbon spacer molecule to the activated surface of the conduit; and
   covalently binding a non-microbicidal acyl-homoserine lactone analog to the at least one hydrocarbon spacer molecule bound to a surface of the conduit, wherein the conduit which is covalently bound to the acyl-homoserine lactone analog via the at least one hydrocarbon tether has a Formula (II),

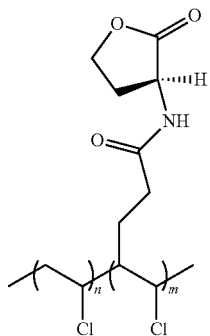

and wherein n or m is a number greater than 1.

6. The method of claim 5, comprising covalently binding a second hydrocarbon spacer molecule to the activated surface of the airway device before covalently binding the non-microbicidal acyl-homoserine lactone analog.

7. The method of claim 5, wherein n is greater than m.

8. The method of claim 7, wherein n is 4 and m is 1.

9. An airway device system comprising:
   a conduit for insertion into a patient's trachea; and
   an acyl-homoserine lactone analog having a hydrocarbon tether covalently bound directly to the conduit, wherein the acyl-homoserine lactone analog is configured to reduce biofilm formation on the conduit when the conduit is inserted into the trachea without killing one or more microorganisms associated with the biofilm formation, wherein the conduit which is covalently bound to the acyl-homoserine lactone analog having a hydrocarbon tether has a Formula (II),

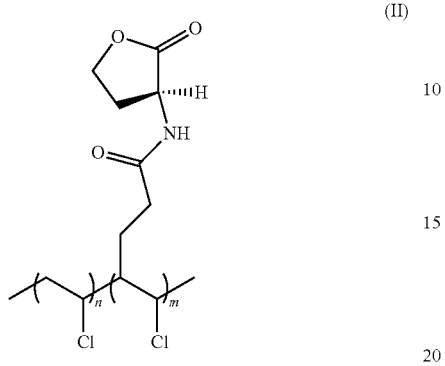

(II)

and wherein n or m is any number greater than 1.

10. The system recited in claim 9, wherein n is greater than m.

11. The system recited in claim 9, wherein n is 4 and m is 1.

12. An airway device, comprising:
a polymeric device body having one or more surfaces comprising a plurality of attachment sites, wherein at least one surface comprises one or more non-microbicidal acyl-homoserine lactone analogs that are directly, covalently attached to a portion of the attachment sites via hydrocarbon tethers, wherein the one or more acyl-homoserine lactone analogs are configured to prevent biofilm formation by interrupting bacterial communication, and wherein the polymeric device body which is covalently attached to the one or more acyl-homoserine lactone analogs via the hydrocarbon tethers has a Formula (II),

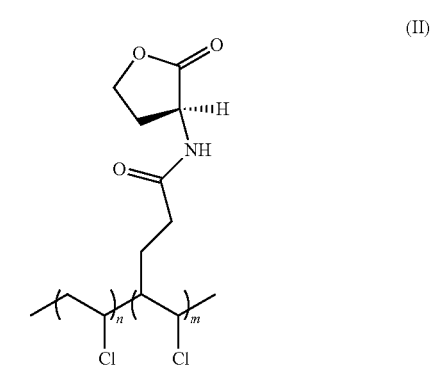

(II)

where m or n is any number greater than 1.

13. The airway device recited in claim 12, wherein the one or more non-microbicidal acyl-homoserine lactone analogs are directly, covalently attached to 1 in 4 of the attachment sites of the one or more surfaces of the polymeric device.

14. The airway device recited in claim 12, wherein n is greater than m.

15. The airway device recited in claim 12, wherein n is 4 and m is 1.

* * * * *